US005720296A

United States Patent [19]
Cha

[11] Patent Number: 5,720,296
[45] Date of Patent: Feb. 24, 1998

[54] APPARATUS AND METHOD FOR ANALYZING BODY COMPOSITION BASED ON BIOELECTRICAL IMPEDANCE ANALYSIS

[76] Inventor: Ki Chul Cha, 351-89 Hwakok 7-Dong Kangseu-Ku, Seoul, Rep. of Korea

[21] Appl. No.: 550,207

[22] Filed: Oct. 30, 1995

[30] Foreign Application Priority Data

Jun. 24, 1995 [KR] Rep. of Korea .......... 95-17226

[51] Int. Cl.$^6$ .......... A61B 5/04
[52] U.S. Cl. .......... 128/734
[58] Field of Search .......... 128/734, 735, 128/774, 639

[56] References Cited

U.S. PATENT DOCUMENTS 4,895,163  1/1990  Libke et al. .
4,911,175  3/1990  Shizgal .
5,335,667  8/1994  Cha et al. .
5,449,000  9/1995  Libke et al. .......... 128/734
5,579,782  12/1996  Masuo .......... 128/734
5,611,351  3/1997  Sato et al. .......... 128/734

Primary Examiner—Francis Jaworski
Attorney, Agent, or Firm—Staas & Halsey

[57] ABSTRACT

An apparatus for analyzing body composition based on bioelectrical impedance analysis, and a method therefor are disclosed. The method for analyzing body composition includes the step of providing eight electrodes for being contacted to a right palm, a right thumb, a left palm, a left thumb, a right front sole, a right rear sole, a left front sole and a left rear sole. Then a switch is selected by a command of a micro-processor so as to form a current path. Then a current is made to flow through said selected electrodes and through a human body to an impedance measuring instrument. Then a switch is selected by a command of said micro-processor so as to form voltage electrodes. Then impedances for respective body portions are measured by means of the impedance measuring instrument. Then impedances of two body portions are decided based on the current and voltage of the impedance measuring instrument. Then the body composition is analyzed based on the measured impedance.

11 Claims, 5 Drawing Sheets

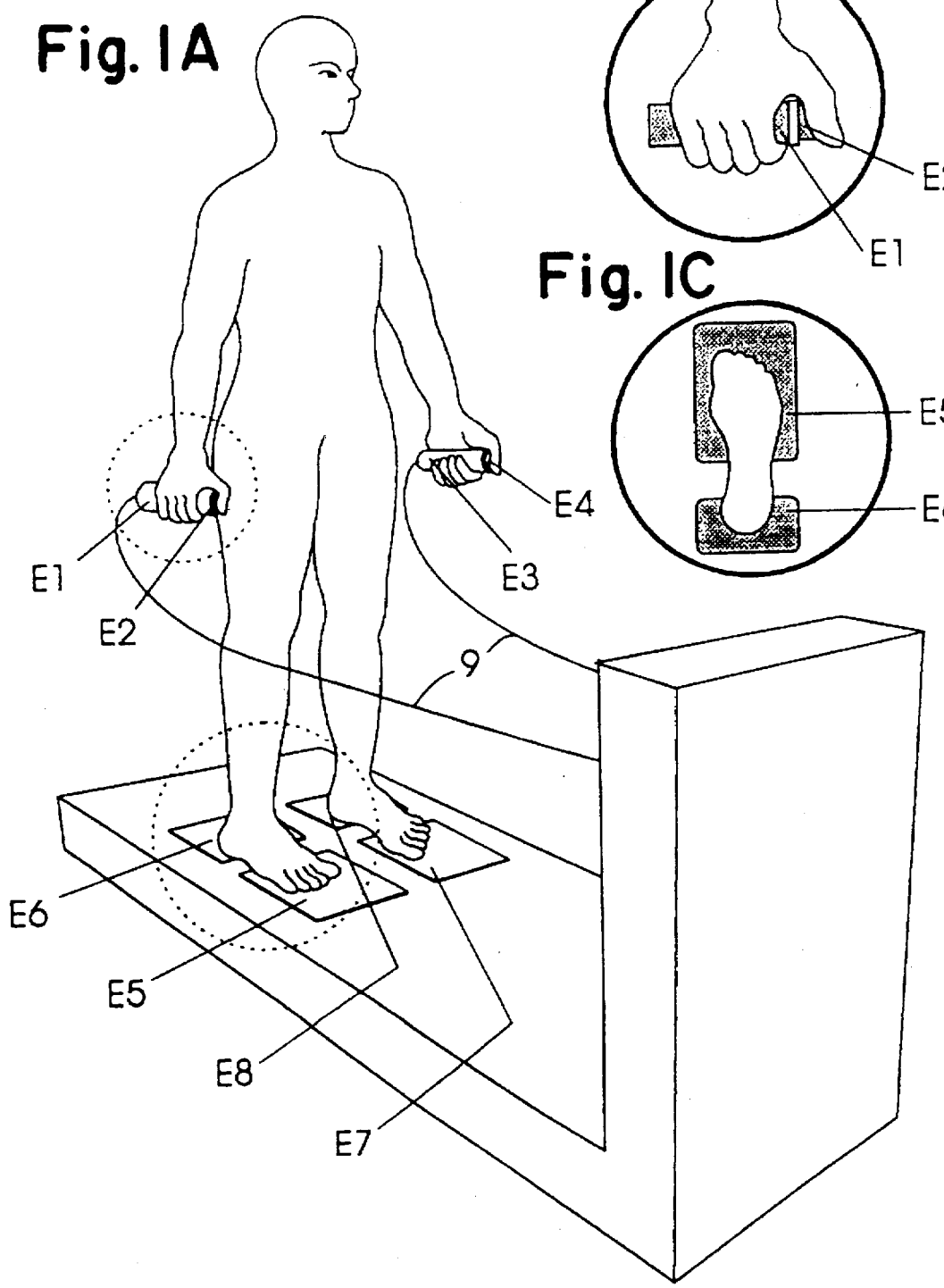
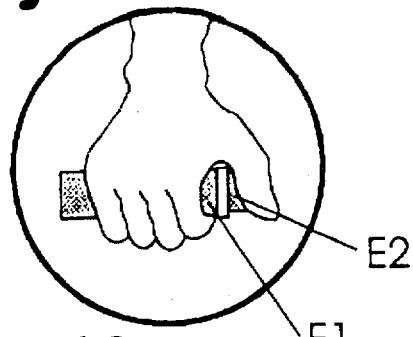
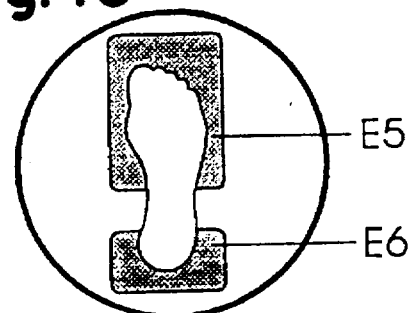

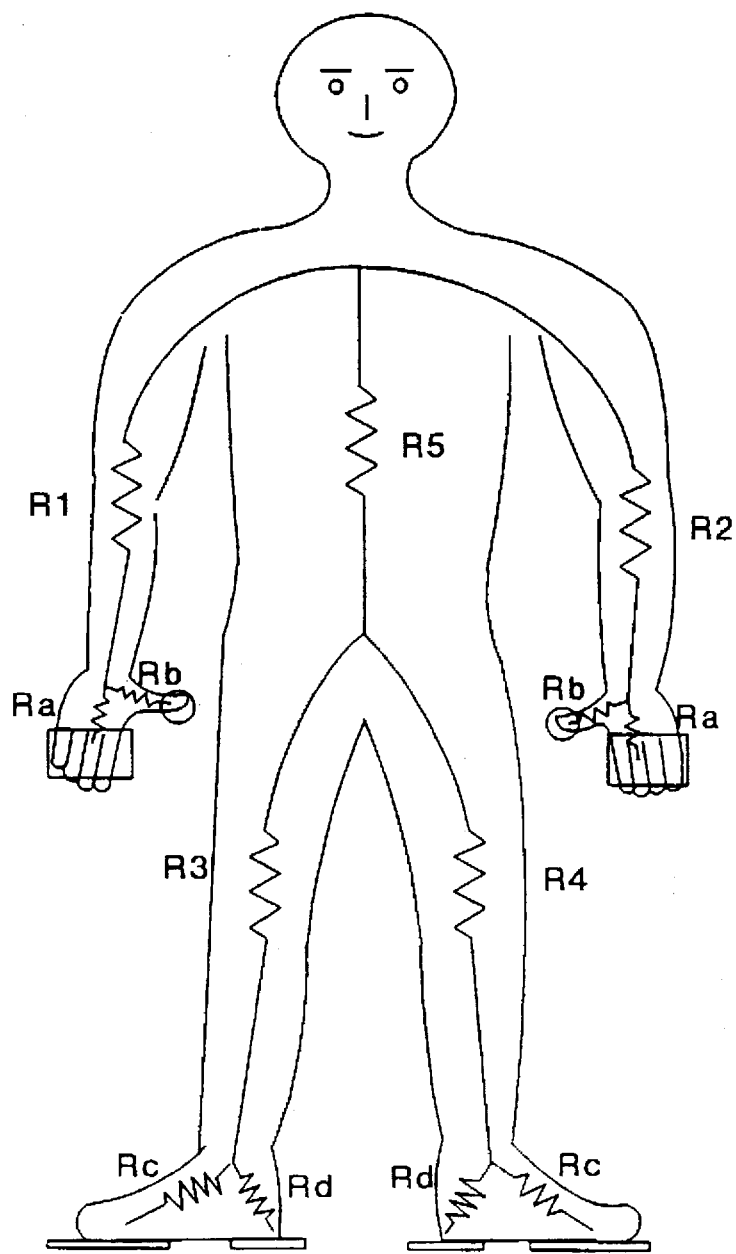

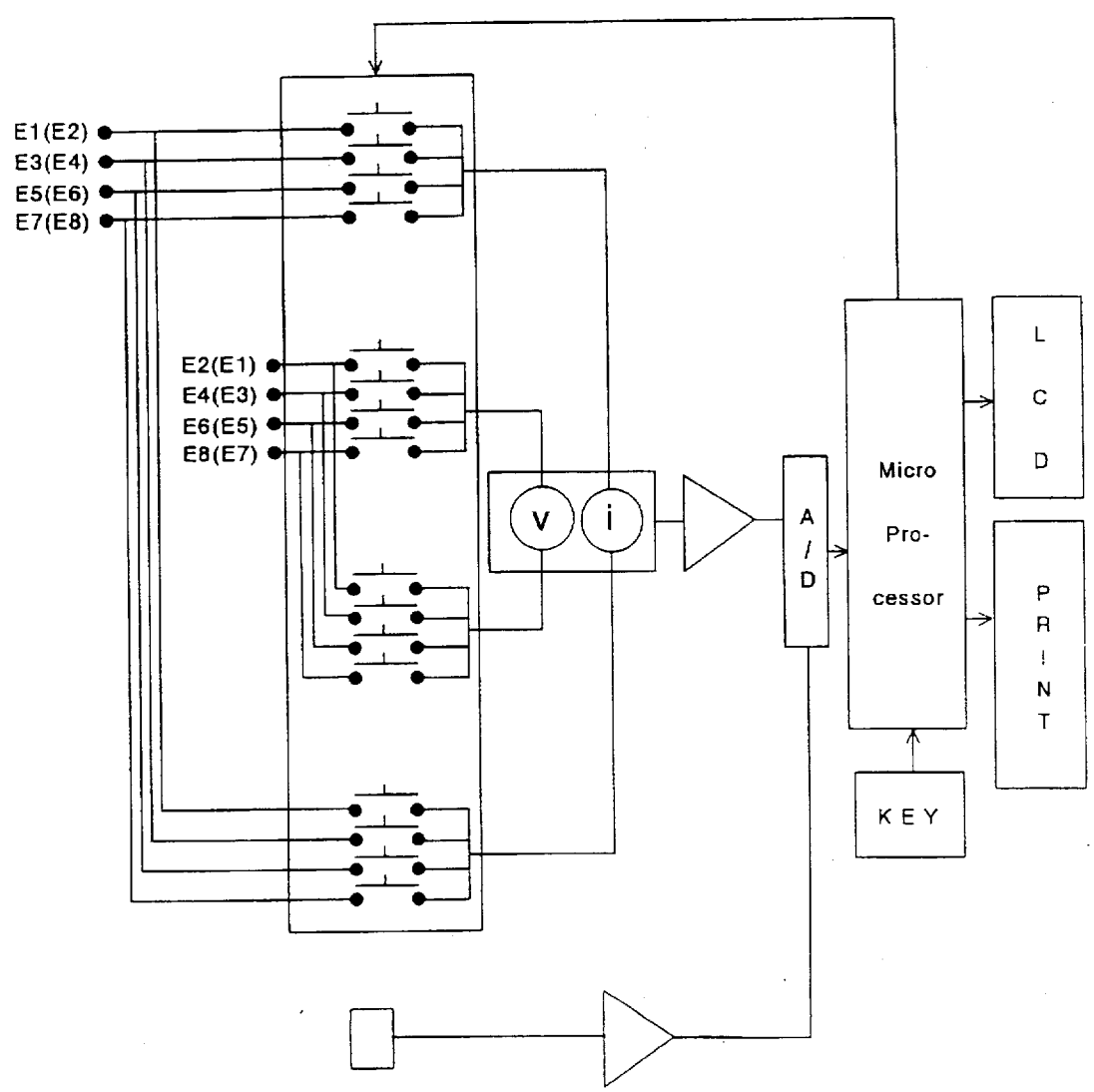

APPARATUS AND METHOD FOR ANALYZING BODY COMPOSITION BASED ON BIOELECTRICAL IMPEDANCE ANALYSIS

FIELD OF THE INVENTION

The present invention relates to an apparatus for analyzing body composition based on bioelectrical impedance analysis, and a method therefor. Particularly, the present invention relates to an apparatus for measuring the impedance of the body segments by contacting the hands and the feet to novel metal electrodes, and a method for quantitatively analyzing body composition such as body fluid, body fat, and the like.

BACKGROUND OF THE INVENTION

A human body is composed of water, protein, bone and fat, in addition to small amounts of special components. The total of these elements constitutes the body weight. Quantitatively measuring the respective elements is called body composition analysis. The proportion occupied by the fat is called fatness and is used in diagnosing various adult diseases. In the medical terms, of the body composition, fat free mass (FFM) is the main component for supporting the human body. Patients suffering from malnutrition related, for example to cancer are subject to a periodic FFM measurement to determine a remission state or monitor progress of the disease. In the case where a fatty man performs athletic exercises to reduce the body weight, it frequently happens that the body weight shows almost no variation within a relatively short period of several months. In this case, if the body composition is measured, it will be found that the amount of muscle has increased, although the amount of fat has decreased. In this way, the effect of the athletic exercise can be measured in a rational manner. Further, based on the analysis of the body composition, the growth of children and the nutritional status of elderly men can be diagnosed. Particularly, for various patients, the segmental water distribution can be measured to determine patient's hydration status.

There are various conventional methods for measuring the body composition. One of them is hydrodensitometry, and this method is carried out in the following manner. That is, the human body is immersed into water, and in this state, the body weight is measured. Then based on the density of the human body, the amount of fat is calculated. This method is based on the principle that fat is lighter than FFM. This measuring method shows a high accuracy, and therefore, it is used as a standard method. However, it has the disadvantage that it is a troublesome task to carry out it, and thus cannot be applied to an elderly man or to a patient.

Another conventional method is to measure the thickness of the sub-cutaneous fat layer by using a caliper or near infrared rays. This method has the disadvantage that the accuracy is low.

Further, there are photographic methods such as nuclear magnetic resonance (NMR), and dual energy X-ray absorptionmetry (DEXA), and a dilution methods such as heavy water (D20) and bromide solution. However, these methods are expensive to carry out, and therefore, they cannot be applied to general patients in an economical manner.

As another method for measuring the body composition, there is bioelectrical impedance analysis (BIA). This method has the advantages that it is safe compared with the other conventional methods, the measuring cost is very low, and the measuring is done in a fast manner. This method is carried out in the following manner. That is, a weak alternating electric current is passed across the human body to measure the electrical resistance or conductance of the body, as well as measuring the height and weight. Based on these measured values, the amount of the body fluid, the fluid balance inside and outside the cell, and the amount of the body fat are calculated.

In U.S. patent application Ser. No. 07/979,791, the analysis method based on the bioelectrical impedance is carried out in the following manner. That is, in a state with a patient lying, contact electrodes are attached on the skin of the body. The electrodes are surface electrodes which are similar to the electrodes for the electro-cardiogram.

In the conventional method, four electrodes which are similar to the electrodes for the electro-cardiographic test are attached on the wrist, back of hand, ankle and back of foot, thereby electrically connecting the human body to an impedance measuring instrument. Then an electric current is let to flow, and thus, the resistance between the wrist and the ankle is measured.

In this method, in a state with a human body lying, the electrodes are attached to the skin of the human body, and then, the impedance of the human body is measured. Then based on the measured values, the results such as percent body fat and the like are obtained by using a computer. Therefore, this method can be carried out only by employing a particularly trained person. Therefore, it cannot be used by the general public in saunas, athletic rooms and the like.

Further, in this method, the impedances of the body segments such as arm, trunk and leg cannot be separately measured, and therefore, the difference between individuals in the regional impedance distribution causes a measurement error.

Further, in this conventional method, the measuring person attaches the electrodes to the body portions of the person to be measured, and therefore, the attachments are not always done to the exact position, thereby generating measuring errors.

Further, if hairs exist on the attachment positions, there is the inconvenience that the hairs have to be removed before attaching the electrodes.

Further, this conventional method has the inconvenience that the body impedance is measured, and then, a computer is used to calculate the fat proportion. That is, the measuring person has to attach the electrodes to the relevant positions of the body of the person to be measured, the body weight and the body height have to be measured separately, and then, a computer has to be used to calculate the fatness. Therefore, it takes much time in carrying out the measuring and analyzing.

In an attempt to overcome the above described disadvantages of the conventional techniques, the present inventor developed an apparatus for analyzing body composition and a method therefor, and filed a patent application under Korean Patent Application No. 94-23440 (filed on Sep. 15, 1994).

The present invention is an improvement of the above invention, in which the different segments of the body impedance can be measured and analyzed in a convenient and precise manner.

OBJECTS OF THE INVENTION

Therefore, it is an object of the present invention to provide an apparatus for analyzing the body composition by measuring the bioelectrical impedance, in which the body composition can be analyzed in a simple and convenient manner even without a specially trained person, like when measuring body weight on an electronic scale.

It is another object of the present invention to provide an apparatus for measuring the body impedance, in which a person can attach his palms of hands and his soles of feet to the electrodes without an assistance of other people, thereby quickly and conveniently connecting an impedance measuring apparatus to the body.

It is still another object of the present invention to provide an apparatus for precisely measuring the segmental body impedance by attaching the palms of hands and the soles of feet to 8 metal plate electrodes.

It is still another object of the present invention to provide an apparatus for analyzing the body composition, in which the body weight can be simultaneously measured, and the body height can be inputted in a simple manner.

It is still another object of the present invention to provide an apparatus for analyzing the body composition, in which the composition analysis results can be known through a display unit immediately, and can be printed simultaneously.

SUMMARY OF THE INVENTION

In achieving the above objects, the apparatus for analyzing the body composition based on the bioelectrical impedance analysis according to the present invention includes:

a plurality of electrodes E1–E8 for contacting with a right palm, a right thumb, a left palm, a left thumb, a right front sole, a right rear sole, a left front sole, and a left rear sole respectively;

an impedance measuring instrument 11 for measuring the impedance based on a voltage-current ratio after making an alternating current flow between two of the electrodes and by reading the voltage difference;

an electronic switch 10 for being controlled by a microprocessor 14 to select electrical connections between the electrodes 1–8 and the impedance measuring instrument a weight measuring sensor 18 for measuring the body weight of the person to be measured;

a keyboard 15 for inputting the body height, age and sex of the person to be measured;

an A/D converter 13 and amplifiers 12 and 19 for interfacing the impedance measuring instrument 11 and the weight sensor 18 to the micro-processor 14;

the micro-processor 14 controlling the electronic switch 10 and processing the data received from the impedance measuring instrument 11 and the keyboard 15; and a display unit 16 for displaying the results.

In the body composition analyzing apparatus of the present invention, the results processed by the microprocessor 14 are displayed on the display unit 16, and when needed, a printer 17 is added for printing the data.

In another aspect of the present invention, the method for measuring the body impedance according to the present invention includes the steps of;

contacting a right palm, a right thumb, a left palm, a left thumb, a right front sole, a right rear sole, a left front sole and a left rear sole to eight electrodes 1–8;

measuring segmental impedances by means of an impedance measuring instrument 11 by selecting an electronic switch 10 which is controlled by a microprocessor 14;

measuring body weight by means of a weight measuring sensor 18;

inputting body height, age and sex through a keyboard 15; and measuring an amount of body fluid (TBW), an amount of fat free mass (FFM), a percent body fat (%BF) and a distribution of body fluid (ECW/ICW), by means of the micro-processor 14.

The results of the analysis can be displayed on a display unit 12 or can be printed through a printer 14.

BRIEF DESCRIPTION OF DRAWINGS

The above objects and other advantages of the present invention will become more apparent by describing in detail the preferred embodiment of the present invention with reference to the attached drawings in which:

FIG. 1 is a schematic view showing a person measuring the body composition by standing on the body composition analyzing apparatus according to the present invention;

FIG. 2 schematically illustrates impedance models of the human body to be measured by the apparatus according to the present invention;

FIG. 3 illustrates the circuit of the body composition analyzing apparatus according to the present invention.

DETAILED DESCRIPTION OF THE PREFERRED EMBODIMENT

Figure 4A:
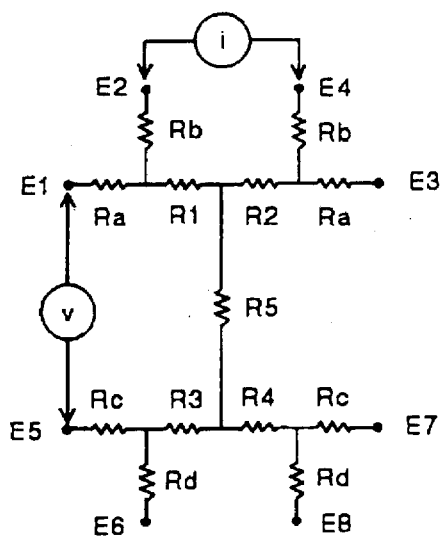
FIGS. 4A to 4H illustrate electric circuits for the measurement of segmental impedance according to the present invention.

FIG. 1 is a schematic view showing a person measuring the body composition by standing on the body composition analyzing apparatus according to the present invention.

The apparatus of the present invention includes: a right palm electrode E1 for being surrounded by a right hand and the fingers excluding the right thumb; a right thumb electrode E2 for contacting with only a right thumb; a left palm electrode E3 for being surrounded by a left palm and the left fingers excluding the left thumb; a left thumb electrode E4 for contacting only with a left thumb, a right front electrode E5 for contacting only with a right front sole; a right rear sole electrode E6 for contacting only with a right rear sole; a left front sole electrode E7 for contacting only with a left front sole; and a left rear sole electrode E8 for contacting only with a left rear sole.

Thus, the body composition analyzing apparatus according to the present invention includes eight electrodes for contacting with eight extremity portions of the human body. A person to be measured stands on the apparatus in an upright posture, and in this state, the hands and feet are contacted to the electrodes. Therefore, the impedance measurement can be carried out in a convenient manner.

The apparatus of the present invention is provided with eight electrodes to contact with eight portions of the human body as described above, and the impedance model of the human body is as shown in FIG. 2.

FIG. 2 schematically illustrates impedance models to be measured by the apparatus according to the present invention.

It will be indicated as follows. That is, the resistance from the right wrist to the joint of the right shoulder is indicated by R1, the resistance from the left wrist to the joint of the left shoulder is indicated by R2, the resistance from the right ankle to the joint of the right hip joint is indicated by R3, the resistance from the left ankle to the joint of the left hip joint is indicated by R4, the resistance of the trunk is indicated by RS, the resistance from the palm to the wrist is indicated by Ra, the resistance from the thumb to the wrist is indicated by Rb, the resistance from the front sole to the ankle is indicated by Rc, and the resistance from the rear sole to the ankle is indicated by Rd.

FIG. 3 illustrates the circuit of the body composition analyzing apparatus according to the present invention.

The apparatus of the present invention is provided with a weight measuring sensor 18 so as to make it possible to measure the body weight of a person. The information on the body weight thus measured is inputted into the micro-processor 14, and then, the body height, age and sex are entered through the keyboard 15, so that the micro-processor 14 can compute the amount of the body fluid (TBW), fat free mass (FFM), and the percent body fat (% BF).

The apparatus for analyzing the body composition based on the bioelectrical impedance method according to the present invention includes:

- a plurality of electrodes E1–E8 for contacting with a right palm, a right thumb, a left palm, a left thumb, a right front sole, a right rear sole, a left front sole, and a left rear sole respectively;
- an impedance measuring instrument 11 for measuring the impedance based on a voltage-current ratio by injecting an alternating current flow between two electrodes and by reading the voltage difference between two electrodes;
- an electronic switch 10 for being controlled by a micro-processor to select electrical connections between the electrodes E1–E8 and the impedance measuring instrument 11;
- a weight measuring sensor 18 for measuring the body weight of the person to be measured:
- a keyboard 15 for inputting the body height, age and sex of the person to be measured;
- an A/D converter 13 and amplifiers 12 and 19 for interfacing the impedance measuring instrument 11 and the weight sensor 18 to the micro-processor 14;
- the micro-processor 14 for controlling the electronic switch 10 and for processing the data received from the impedance measuring instrument 11 and the keyboard 15; and
- a display unit 16 for displaying the processed results.

In the body composition analyzing apparatus of the present invention, the results processed by the micro-processor 14 are displayed on the display unit 16, and when needed, a printer 17 is added for printing the data.

FIGS. 4A to 4H illustrate electric circuits representing the regional impedances of a human body to be measured according to the present invention.

Referring to FIGS. 3 and 4, the resistances of the different body portions R1, R2, R3, R4, R5 will be described in detail as to how they are measured.

As shown in FIG. 4A, the electronic switch 10 is connected between electrodes E2 and E4 by a command of the micro-processor 14, so that an electric current would flow between the electrodes E2 and E4. Further, the electronic switch 10 is connected between electrodes E1 and E5 by a command of the micro-processor 14, so that the voltage between the electrodes E1 and E5 can be measured. Thus the resistance R1 can be obtained from the above mentioned current and voltage.

Figure 4B:
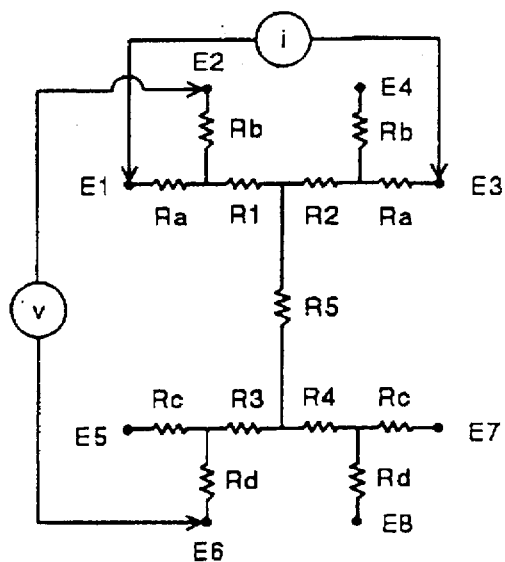

As shown in FIG. 4B, the electronic switch 10 is connected between electrodes E1 and E3 by a command of the micro-processor 14, so that a current would flow between the electrodes E1 and E3. Further, the electronic switch 10 is connected between electrodes E2 and E6 by a command of the micro-processor 14, so that the voltage between the electrodes E2 and E6 can be measured. Then the value of the resistance R1 can be obtained from the current and voltage.

Figure 4C:
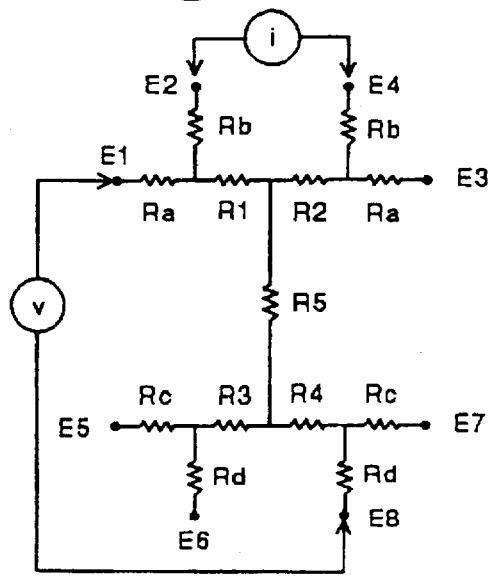

As shown in FIG. 4C, the electronic switch 10 is connected between electrodes E2 and E4 by a command of the micro-processor 14, so that a current would flow between the electrodes E2 and E4. Further, the electronic switch 10 is connected between electrodes E1 and E8 by a command of the micro-processor 14, so that the voltage between the electrodes E1 and E8 can be measured. Then the value of the resistance R1 can be obtained from the current and voltage.

Figure 4D:
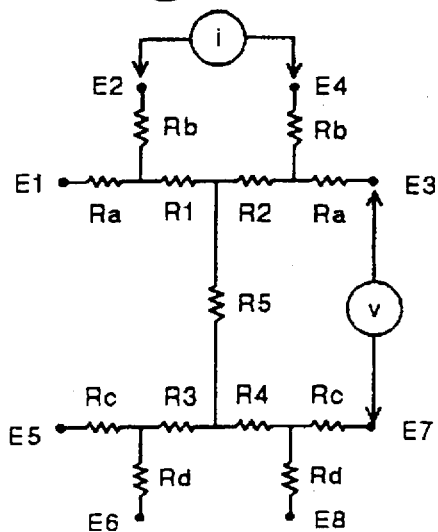

As shown in FIG. 4D, the electronic switch 10 is connected between the electrodes E2 and E4 by a command of the micro-processor 14, so that a current would flow between the electrodes E2 and E4. Further, the electronic switch 10 is connected between electrodes E3 and E7 by a command of the micro-processor 14, so that the voltage between the electrodes E3 and E7 can be measured. Then the value of the resistance R2 can be obtained from the current and the voltage.

Figure 4E:
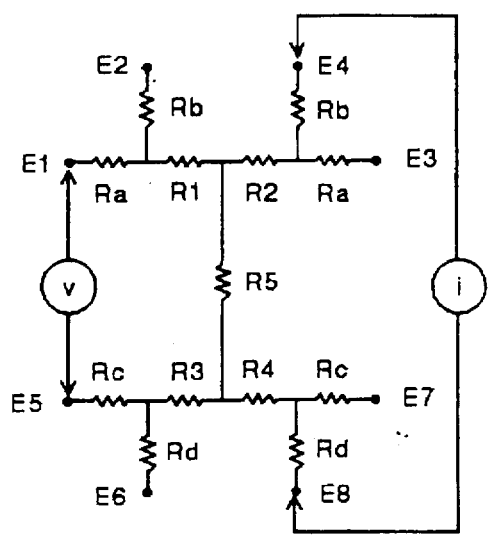

As shown in FIG. 4E, the electronic switch 10 is connected between electrodes E4 and E8 by a command of the micro-processor 14, so that a current would flow between the electrodes E4 and E8. Further, the electronic switch 10 is connected between electrodes E1 and E5 by a command of the micro-processor 14, so that the voltage between the electrodes E1 and E5 can be measured. Then the value of the resistance R5 can be obtained from the current and the voltage.

Figure 4F:
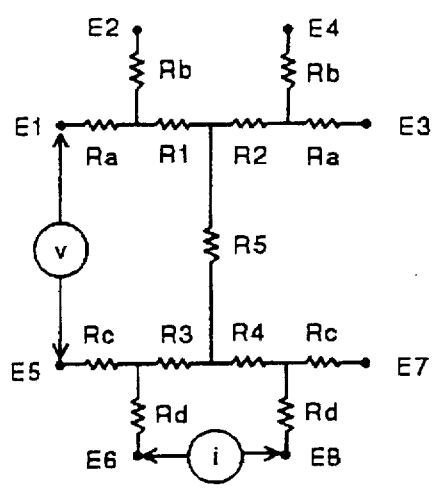

As shown in FIG. 4F, the electronic switch 10 is connected between electrodes E6 and E8 by a command of the micro-processor 14, so that a current would flow between the electrodes E6 and E8. Further, the electronic switch 10 is connected between electrodes E1 and E5 by a command of the micro-processor 14, so that the voltage between the electrodes E1 and E5 can be measured. Then the value of the resistance R3 can be obtained from the current and the voltage.

Figure 4G:
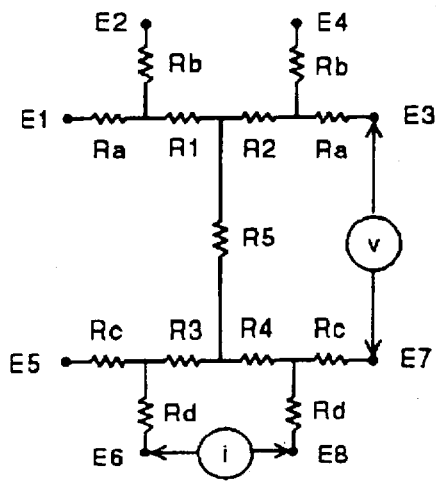

As shown in FIG. 4G, the electronic switch 10 is connected between electrodes E6 and E8 by a command of the micro-processor 14, so that a current would flow between the electrodes E6 and E8. Further, the electronic switch 10 is connected between electrodes E3 and E7 by a command of the micro-processor 14, so that the voltage between the electrodes E3 and E7 can be measured. Then the value of the resistance R4 can be obtained from the current and the voltage.

Figure 4H:
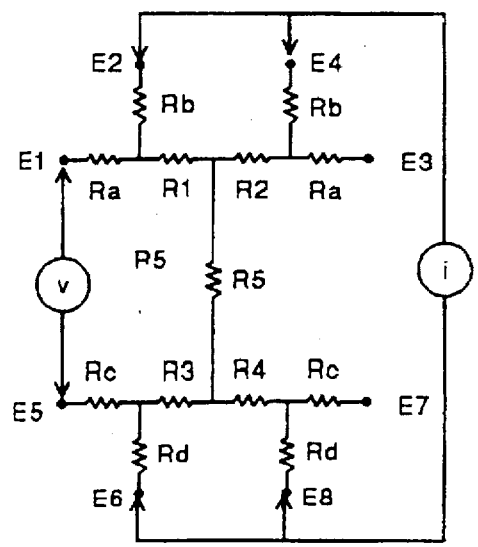

As shown in FIG. 4H, the electronic switch 10 is connected between electrodes E2 and E4 by a command of the micro-processor 14, so that a current would flow between the electrodes E2 and E4. Further, the electronic switch 10 is connected between electrodes E3 and E7 by a command of the micro-processor 14, so that the voltage between the electrodes E3 and E7 can be measured. Then the value of the resistance of the whole human body can be obtained from the current and the voltage.

FIGS. 4A to 4H illustrate only exemplary cases for measuring the impedances by making a current flow between two electrodes among the electrodes E1 to E8 and by measuring the voltage between other two electrodes. Besides these examples, there can be other examples of measuring the impedances of the body segments.

In the present invention, the impedance measuring instrument 11 is connected to the eight electrodes E1–E8. The eight electrodes E1–E8 serve as current electrodes. The eight electrodes E1-E8 serve as current electrodes and voltage electronic switch 10 by a command of the micro-processor 14, in such a manner that they should serve different functions. For example, if the electrode E1 is a current electrode, then the electrode E2 is a voltage electrode, while if the electrode E2 is a current electrode, the electrode E1 is a voltage electrode. The electrodes E3 and E4 are also used in such a manner that they should serve different functions, and the electrodes E5 and E6 are also used in the same manner, while the electrodes E7 and E8 are also used in the same manner.

That is, each of the electrodes E1-E8 serves as a current electrode or a voltage electrode. As shown in FIG. 3, if the electrodes E1, E3, E5 and E7 are used as current electrodes, then the electrodes E2, E4, E6 and E8 are used as voltage electrodes. On the other hand, if the electrodes E2, E4, E6 and E8 are used as current electrodes, then the electrodes E1, E3, E5 and E7 are used as voltage electrodes.

In the impedance measuring method of the present invention, the variations is the values of the resistances Ra, Rb, Rc and Rd do not affect the measured values of the impedances of the different body portions. That is, when a person to be measured steps on the electrodes E5-E8 with the both feet, and holds electrodes E1-E4 with the both hands, even if the contact positions between the electrodes and the body are slightly shifted, it does not affect the measured resistance values R1-R5.

In measuring the impedances of the different body segments, the electrical connections between the electrodes E1-E8 and the impedance measuring instrument 11 have to be changed many times based on the segmental measurement described above. In order to automatize this, there is the electronic switch 10 which is opened/closed by the micro-processor 14.

Meanwhile, the body weight is measured by a weight measuring sensor 18 which is placed under the foot electrodes E5-E8 of the body composition analyzing apparatus of the present invention. The measured body weight is transferred through the amplifier 19 and the A/D converter 17 to the micro-processor 14. The resistance values R1-R5 which are measured by the impedance measuring instrument 11 also are transferred through the amplifier 12 and the A/D converter 17 to the micro-processor 14.

Then body height, age and sex are inputted through the keyboard 15, and these data are transferred through an interface to the micro-processor 14. Based on the impedances, the body height, weight, age and sex which are stored in the micro-processor 14, the body composition such as the amount of the body fluid (TBW), the fat free mass (FFM), the body fat proportion(% BF), and the body fluid distribution ratio inside and outside the cells are analyzed. The analyzed results are displayed on the display unit 16, and printed by the printer 17.

Examples for computing the body composition from the measured impedances are as follows. It is assumed that the left and right arms and legs and the trunk are five cylindrical conductors which have uniform cross sectional areas and which are similar in length. Based on this assumption, impedances R1-R5 are measured. The parallel connection value Rarm for both arms is defined as follows.

$$Rarm=(R1 \times R4)/(R3+R4) \quad (I)$$

The parallel connection value Rleg for the both legs is defined as follows.

$$Rleg=(R3 \times R4)/(R3+R4) \quad (II)$$

The resistance value for the trunk Rtrunk is defined to be R5.

The amount of water contained in a body segment is proportional to $Ht^2/R$, where R indicates the impedance value for the relevant body segment, and Ht indicates the body height of the measuring person.

The total body water (TBW) is the sum of the segmental water, and is defined as follows.

$$TBW=C_1.Ht^2/Rarm+C_2.Ht^2/Rleg+C_3.Ht^2/Rtrunk+C_4 \quad (III)$$

In formula III above, $C_1$, $C_2$, $C_3$, and $C_4$ are the best suitable constants, and can be obtained from TBW which is obtained by a heavy water dilution method ($D_2O$ dilution).

Formula III is stored in the micro-processor 14, and therefore, TBW can be obtained from the calculated Rarm, Rleg, Rtrunk and Ht.

In addition to these variables, sex and age can be used as additional valuables.

$$TBW=C_1.Ht^2/Rarm+C_2.Ht^2/Rleg+C_3.Ht^2/Rtrunk+C_4.Sex+C_5.Age+C_6 \quad (IV)$$

In the above formula, Sex, 0 is inputted for female, and 1 is inputted for male, while Age is the age of the person to be measured.

Body fat contains relatively small amount of water, and therefore, this water content is disregarded. The fat free mass (FFM) contains about 73% of water, and therefore, (FFM) is defined as follows.

$$FFM=TBW/0.73 \quad (V)$$

The amount of body fat (FAT) is defined to be the weight (Wt) minus FFM, and is defined by formula VI, thus percent body fat (%BF) is defined by formula VII.

$$FAT=Wt-FFM \quad (VI)$$

$$\% BF=(Wt-FFM) \times 100/Wt \quad (VII)$$

According to the present invention as described above, even without assistance of a specially trained person, the measuring person can stand with the two legs on the electrodes, and can grasp the electrode rods with two hands, so that the right palm, the right thumb, the left palm, the left thumb, the right front sole, the right rear sole, the left front sole and the left rear sole would be contacted with 8 different electrodes. Thus the impedances of the different body portions are automatically measured by the eight electrodes, and the body composition is analyzed in a precise and simple manner.

It should be apparent to those skilled in the art that various changes and modifications can be added to the present invention without departing from the scope of the present invention which is limited only by the appended claims.

What is claimed is:

1. A method for analyzing human body composition, comprising:
    (a) providing eight electrodes to contact a right palm, a right thumb, a left palm, a left thumb, a right front sole, a right rear sole, a left front sole and a left rear sole;
    (b) providing a current generator with two current terminals between which a current is generated;
    (c) providing a voltage meter with two voltage terminals between which a voltage drop is measured;
    (d) providing a set of automatic electronic switches which make connections and disconnections between said electrodes and said terminals;
    (e) measuring the impedances of all body segments including a right leg impedance, a left leg impedance, a right arm impedance, a left arm impedance, and a trunk impedance without performing any calculations; and (g) analyzing body composition based on the measured impedances of the body segments.

2. The method as claimed in claim 1, wherein four of said electrodes are used as current electrodes while the remaining four of said electrodes are used as voltage electrodes.

3. The method as claimed in claim 1, further comprising measuring body weight by using a weight measuring sensor to input the sensed data into a micro-processor.

4. The method as claimed in claim 1, further comprising inputting body height, age and sex of a measuring person through a keyboard into a micro-processor.

5. The method as claimed in claim 1, further comprising displaying the analyzed values for body composition to a picture display.

6. The method as claimed in claim 5, further comprising printing the data of said picture display to a printer.

7. An apparatus for analyzing human body composition based on a bioelectrical impedance method, comprising:

a plurality of electrodes for contacting with a right palm, a right thumb, a left palm, a left thumb, a right front sole, a right rear sole, a left front sole, and a left rear sole respectively;

an impedance measuring instrument for measuring the impedance based on a voltage-current ratio after an alternating current flows between any two of said electrodes and by reading the voltage difference between said any two of said electrodes;

a micro-processor;

an electronic switch being controlled by said microprocessor to select electrical connections between said electrodes and said impedance measuring instrument;

a weight measuring sensor to measure a body weight of a person to be measured;

a keyboard to input the body height, age and sex of the human body being measured;

an A/C converter and amplifiers to interface said impedance measuring instrument and said weight sensor to said micro-processor; and said micro-processor controlling said electronic switch and processing the data received from said impedance measuring instrument and said keyboard.

8. The apparatus as claimed in claim 7, further comprising a display unit to display the results processed by said micro-processor.

9. The apparatus as claimed in claim 8, further comprising a printer to print results processed by said micro-processor.

10. The apparatus as claimed in claim 7, wherein the electrodes for contacting with the right thumb and right palm are adapted to be grasped with the right hand, and the electrodes for contacting with the left thumb and left palm are adapted to be grasped with the left hand, and are connected through a flexible wire to a main body of the apparatus.

11. The method as claimed in claim 1, wherein said right palm electrode and said right front sole electrode are connected to current terminals and said right thumb electrode and said left thumb electrode are connected to voltage terminals to measure an impedance of a right arm;

wherein said left palm electrode and said left front sole electrode are connected to current terminals and said left thumb electrode and said right thumb electrode are connected to voltage terminals to measure an impedance of a left arm;

wherein said right palm electrode and said right front sole electrode are connected to current terminals and said left thumb electrode and said left rear sole electrode are connected to voltage terminals to measure an impedance of a trunk;

wherein said right palm electrode and said right front sole electrode are connected to current terminals and said right rear sole electrode and said left rear sole electrode are connected to voltage terminals to measure an impedance of a right leg, and wherein said left palm electrode and said left front sole electrode are connected to current terminals and said left rear sole electrode and said right rear sole electrode are connected to voltage terminals to measure an impedance of a left leg.

* * * * *